(12) United States Patent
Lindigkeit

(10) Patent No.: US 7,166,256 B2
(45) Date of Patent: Jan. 23, 2007

(54) NONPRECIOUS DENTAL CASTING ALLOY

(75) Inventor: Jürgen Lindigkeit, Königsbach-Stein (DE)

(73) Assignee: J.P. Winkelstroeter KG, Ispringen (DE)

(*) Notice: Subject to any disclaimer, the term of this patent is extended or adjusted under 35 U.S.C. 154(b) by 224 days.

(21) Appl. No.: 10/606,937

(22) Filed: Jun. 27, 2003

(65) Prior Publication Data

US 2004/0129349 A1 Jul. 8, 2004

(30) Foreign Application Priority Data

Jul. 13, 2002 (DE) .............................. 102 31 737

(51) Int. Cl.
C22C 19/07 (2006.01)

(52) U.S. Cl. .................................................. 420/436

(58) Field of Classification Search ............... 420/437, 420/436; 75/246
See application file for complete search history.

(56) References Cited

U.S. PATENT DOCUMENTS

| | | | |
|---|---|---|---|
| 2,763,547 A | | 9/1956 | Dyrkacz et al. |
| 3,837,838 A | * | 9/1974 | Mohammed ................. 420/585 |
| 3,865,585 A | * | 2/1975 | Rademacher .............. 420/436 |
| 4,116,724 A | | 9/1978 | Hirschfeld et al. |
| 4,436,697 A | * | 3/1984 | Friedrich et al. ........... 420/440 |
| 4,459,263 A | * | 7/1984 | Prasad ....................... 420/437 |
| 4,483,821 A | * | 11/1984 | Prasad ....................... 420/437 |
| 4,491,561 A | * | 1/1985 | Mann ........................ 420/437 |
| 4,606,887 A | * | 8/1986 | Hausselt et al. ............ 420/437 |
| 4,728,495 A | * | 3/1988 | Rademacher .............. 420/583 |
| 4,830,824 A | | 5/1989 | Lindigkeit |
| 5,039,574 A | * | 8/1991 | Kulmburg .................. 428/433 |
| 5,227,131 A | | 7/1993 | Weigand |
| 5,228,131 A | * | 7/1993 | Ueda et al. ................ 712/240 |
| 5,556,420 A | * | 9/1996 | Mortazavi et al. ............ 607/9 |
| 5,799,386 A | * | 9/1998 | Ingersoll et al. .......... 29/527.5 |
| 6,656,420 B2 | | 12/2003 | Prasad et al. |
| 6,756,012 B2 | * | 6/2004 | Prasad ....................... 420/436 |
| 7,041,251 B2 | * | 5/2006 | Lindigkeit .................. 420/436 |
| 2002/0004018 A1 | * | 1/2002 | Prasad et al. ............... 420/512 |
| 2002/0041820 A1 | * | 4/2002 | Prasad ....................... 420/437 |
| 2004/0109785 A1 | | 6/2004 | Lindigkeit |

FOREIGN PATENT DOCUMENTS

| | | | |
|---|---|---|---|
| DE | 1 984 538 | | 4/1968 |
| DE | 36 09 184 C2 | | 9/1987 |
| DE | 41 23 606 | | 1/1993 |
| DE | 198 15 091 | | 10/1998 |
| DE | 19845638 C1 | * | 4/2000 |
| EP | 0 509 910 A1 | | 4/1992 |
| FR | 2 733 416 | | 10/1996 |
| JP | 53-31520 | * | 3/1978 |

OTHER PUBLICATIONS

The American Heritage Dictionary of the English Language, 1976, pp. 184 and 243.

* cited by examiner

Primary Examiner—Roy King
Assistant Examiner—Michael P. Alexander
(74) Attorney, Agent, or Firm—Leydig, Voit & Mayer, Ltd.

(57) ABSTRACT

In order to provide an alloy which, on the one hand, can be used for the synthesis of crown and bridge frameworks that may be provided with a tooth-colored veneer of ceramic material, and, on the other hand, enable the synthesis of model casting bases, a nonprecious metal dental casting alloy is provided which substantially consists of:

| | |
|---|---|
| 26–35 wt % | Cr |
| 2–6 wt % | Mo |
| 3–12 wt % | W |
| 0.8–1.5 wt % | Si |
| up to 0.3 wt % | Mn |
| 0.1–0.35 wt % | N |
| <0.1 wt % | Ni |
| 0.2–1.5 wt % | Ta | and manufacturing impurities of <0.1 wt % in each case, remainder cobalt,
the content of tungsten being always greater than the content of molybdenum.

4 Claims, No Drawings

NONPRECIOUS DENTAL CASTING ALLOY

The invention relates to a nonprecious dental casting alloy.

Alloys to be used in dentistry must satisfy special general requirements. For example, burning-on alloys for powder metallurgy must be compatible with commercial dental ceramics as regards thermal expansion and contraction.

In addition, these alloys must be capable of forming a thin oxide layer guaranteeing adhesion between metallic and ceramic surfaces.

In addition, the color of the oxide may not show through the opaque porcelain for esthetic reasons.

In the case of dental castings that are not to be veneered, eg, removable prostheses with clips, a certain activation capacity and resilient hardness are required. Another particularly important factor in dentistry is that processing of the alloys used should be possible in the dental laboratory using available means, ie they should be capable of being cast with conventional casting centrifuges. Furthermore, those dental casting alloys are to be preferred whose hardness in the cast state does not deviate to an extensive degree from the hardness of natural dental enamel so that no appreciable abrasive wear of the tooth is caused by contact of the dental casting alloy with the surface of the tooth. Furthermore, it is advantageous when the alloy can be produced with a low nickel content so that patients who are allergic to nickel can also be provided with such prostheses.

Co/Cr-based casting alloys have been used for so-called prosthetic model casts since 1935. As from ca 1980, such alloys based on cobalt-chromium have also been developed into alloys for crown and bridge frameworks which can be provided with a tooth-colored veneer of ceramic material. In order to adapt model casting alloys to the requirements of ceramic veneering, a usual metallurgical measure has been to remove carbon from these alloys, since the use of frameworks firmly cemented in the mouth does not call for such a high degree of hardness of the model casting alloys, which would, rather, impede dental processing. For example, DE 36 09 184 C2 mentions in this context a maximum carbon content of 0.05 wt %.

Alloys used in model casting work must, on the other hand, satisfy greater demands of hardness and tensile strength, particularly flexural strength. Special binding agents have already been proposed in this context, by means of which specific and conventional model casting alloys can be ceramically veneered despite the high coefficients of thermal expansion, but the carbon present in the conventional model casting alloys in a concentration of up to 0.6% causes coarsening of the carbides during firing and thus leads to deterioration of the mechanical properties.

Such binding agents are, further, not resistant to corrosion.

Common model casting alloys exhibit, unlike veneerable alloys for crowns and bridges, a coefficient of thermal expansion of from 15.5 to $16 \cdot 10^{-6}$ $K^{-1}$ and are thus not suitable for a porcelain veneer (cf, eg, Siebert, Dentallegierungen in der zahnärtzlichen Prothetik, C. Hanser Verlag 1989, page 38). Due to the fact that the thermal expansion properties of the metal and porcelain do not match, stresses occur which find relaxation in spalling or retarded spalling.

It is an object of the present invention to provide an alloy which can be used for making crown and bridge frameworks that can be provided with a tooth-colored ceramic veneer, on the one hand, and which can be used for making model casting bases, on the other hand.

According to the invention, this object is achieved by a nonprecious dental casting alloy, substantially comprising:

| | | |
|---|---|---|
| 25–35 | wt % | Cr |
| 2–6 | wt % | Mo |
| 3–12 | wt % | W |
| 0.8–1.5 | wt % | Si |
| up to 0.3 | wt % | Mn |
| 0.1–0.35 | wt % | N |
| <0.1 | wt % | Ni |
| 0.2–1.5 | wt % | Ta | and manufacturing impurities of <0.1 wt % in each case, remainder cobalt, the content of tungsten being always greater than the content of molybdenum.

The alloy of the invention is an alloy which can be used both for making crown and bridge frameworks that can be veneered with odontoceramic materials, and for making model casting bases.

In particular, the alloy of the invention can be produced without the inclusion of carbon. To this end, the content of C should be <0.05 wt %. The result is that the alloy of the present invention also shows very good laser-weldability.

Freedom from carbon may be easily realized without detriment to the mechanical properties of the present alloy when used for both purposes, ie for making ceramic-veneerable basic constructions and for the production of model casts, ie basic constructions for removable dentures containing nonveneered metal components such as retentive clasps.

Dental alloys free from carbon have been described (cf DE 198 45 638) which are suitable for use as materials for dental prosthetics, particularly for the production of suprastructures. But parts made from these alloys are not suitable for ceramic veneering, as is readily noticeable to the person skilled in the art.

Another alloy is disclosed in DE 41 23 606 C2 which is likewise suitable for the production of castings for crowns, bridges, and models. The coefficient of thermal expansion stated in said reference shows that this alloy is suitable for ceramic veneers. However, it differs from the alloy of the invention and must, in particular, contain rare-earth elements to an extent of from 0.15 to 0.35 wt %, which is a disadvantage in a different aspect of the present invention, namely the desire to be able to produce this alloy by extrusion.

It is known to the person skilled in the art that alloys having a content of rare earth metals cannot be produced by extrusion since the lanthanoid elements do not guarantee consistent analysis results due to their fusion loss characteristics. When production is effected by extrusion casting, however, the process involves keeping the metal alloy in the liquid state for a number of hours up to half a day, so that the fusion losses of the alloying elements are considerable.

The present alloy can now be produced free from rare-earth elements, ie it requires no content of rare earth metals to enable adjustment of desirable mechanical and other properties.

The low modulus of elasticity of the alloys according to DE 41 23 606 C2 furthermore shows that these are not suitable for the synthesis of clasp dental prostheses, as is the alloy of the invention.

The production of the alloys by extrusion casting has the great advantage that the resultant products are cylindrical and can thus be subsequently processed at low cost.

The invention finally relates to the use of the alloy of the invention, as described above, for the production of prosthetic constructions to be veneered with tooth-colored ceramic materials.

Another aspect of the present invention relates to the use of the alloy described above for the production of model casting bases.

Finally, the invention relates, according to another aspect, to a process for the production of a dental casting alloy which is free from nonprecious metals and can be produced by extrusion casting methods.

An exemplary alloy has the following composition:

| | | |
|---|---|---|
| Co | 58.5 | wt % |
| Cr | 30.7 | wt % |
| Mo | 3.1 | wt % |
| W | 5.0 | wt % |
| Mn | 0.03 | wt % |
| Si | 1.3 | wt % |
| N | 0.2 | wt % |
| Ta | 1 | wt % |

It is important for the alloy of the invention to have a content of tungsten which is always greater than the content of molybdenum.

The mechanical properties found on the alloy of the invention according to above example are summarized in the following table:

| | |
|---|---|
| Tensile stress at a given elongation $R_P$ 0.2 (MPa) | 707 |
| Tensile strength Rm (MPa) | 892 |
| Flexural strength A5 (%) | 7.8 |
| Vickers hardness HV 10 | 336 |
| Modulus of elasticity E (GPa) | 219 |
| Laminating strength (ISO 9693) with Carmen ®-Verblendkeramik (sold by Esprident GmbH) | 49.18 MPa |

The invention claimed is:

1. A nonprecious metal dental casting alloy consisting of

| | | |
|---|---|---|
| 25–35 | wt % | Cr |
| 2–6 | wt % | Mo |
| 3–12 | wt % | W |
| 0.8–1.5 | wt % | Si |
| up to 0.3 | wt % | Mn |
| 0.1–0.35 | wt % | N |
| <0.1 | wt % | Ni |
| 0.2–1.5 | wt % | Ta | and manufacturing impurities of <0.1 wt % in each case, wherein the remainder is cobalt, and the content of tungsten (W) is always greater than the content of molybdenum.

2. A method for production of prosthetic constructions comprising veneering the alloy of claim 1 with tooth-colored ceramic bodies.

3. A method for the production of model casting bases comprising casting the alloy of claim 1.

4. A process for the production of an alloy comprising extrusion casting the nonprecious dental casting alloy of claim 1.

* * * * *

UNITED STATES PATENT AND TRADEMARK OFFICE
CERTIFICATE OF CORRECTION

PATENT NO. : 7,166,256 B2
APPLICATION NO. : 10/606937
DATED : January 23, 2007
INVENTOR(S) : Jürgen Lindigkeit It is certified that error appears in the above-identified patent and that said Letters Patent is hereby corrected as shown below:

Title page, item [73]
The assignee should be:

DENTAURUM J.P. Winkelstroeter KG
Turnstrasse 31
Ispringen, Germany D-75228

Signed and Sealed this

Twenty-eighth Day of August, 2007

JON W. DUDAS
*Director of the United States Patent and Trademark Office*